(12) United States Patent
Lellouche et al.

(10) Patent No.: US 11,065,408 B2
(45) Date of Patent: Jul. 20, 2021

(54) METHOD FOR DELIVERY OF BREATHING GAS TO A PATIENT AND SYSTEM FOR PERFORMING SAME

(71) Applicants: UNIVERSITÉ LAVAL, Quebec (CA); UNIVERSITÉ DE BRETAGNE OCCIDENTALE, Brest (FR); OXY'NOV INC, Quebec (CA)

(72) Inventors: Francois Lellouche, Lac Beauport (CA); Erwan L'Her, Brest (FR); Benoit Gosselin, Lac Beauport (CA); Quang-Thang Nguyen, Binh Dinh (VN)

(73) Assignees: UNIVERSITÉ LAVAL, Quebec (CA); UNIVERSITÉ DE BRETAGNE OCCIDENTALE, Brest (FR); OXY'NOV INC, Quebec (CA)

( * ) Notice: Subject to any disclaimer, the term of this patent is extended or adjusted under 35 U.S.C. 154(b) by 429 days.

(21) Appl. No.: 15/765,429

(22) PCT Filed: Oct. 4, 2016

(86) PCT No.: PCT/CA2016/051153
§ 371 (c)(1),
(2) Date: Apr. 2, 2018

(87) PCT Pub. No.: WO2017/059530
PCT Pub. Date: Apr. 13, 2017

(65) Prior Publication Data
US 2018/0280645 A1    Oct. 4, 2018

Related U.S. Application Data

(60) Provisional application No. 62/237,252, filed on Oct. 5, 2015.

(51) Int. Cl.
*A61M 16/00*    (2006.01)
*A61M 16/16*    (2006.01)
(Continued)

(52) U.S. Cl.
CPC ......... *A61M 16/024* (2017.08); *A61B 5/0816* (2013.01); *A61B 5/14551* (2013.01);
(Continued)

(58) Field of Classification Search
None
See application file for complete search history.

(56) References Cited

U.S. PATENT DOCUMENTS

2004/0159323 A1    8/2004    Schmidt et al.
2005/0098178 A1    5/2005    Banner et al.
(Continued)

FOREIGN PATENT DOCUMENTS

EP    0656216 A2    6/1995
WO    2008148134 A1    12/2008

OTHER PUBLICATIONS

International Search Report and Written Opinion for PCT/CA2016/051153, dated Jan. 13, 2017 (9 pages).
(Continued)

*Primary Examiner* — Margaret M Luarca
(74) *Attorney, Agent, or Firm* — Eversheds Sutherland (US) LLP

(57) ABSTRACT

A method for controlling the delivery of a breathing gas to a patient. The method comprises: delivering a flow of breathing gas to a patient, the breathing gas having a breathing gas flowrate and a fraction of inspired oxygen; measuring an oxygen saturation level of the patient; determining a respiratory rate of the patient; automatically adjusting the fraction of inspired oxygen of the breathing gas based on the measured oxygen saturation level of the patient
(Continued)

and a breathing gas flowrate set-point; and automatically adjusting the breathing gas flowrate set-point based on the determined respiratory rate of the patient.

15 Claims, 8 Drawing Sheets

(51) Int. Cl.
*A61B 5/08* (2006.01)
*A61M 16/12* (2006.01)
*A61B 5/00* (2006.01)
*A61B 5/1455* (2006.01)
*A61M 16/10* (2006.01)
*G16H 40/63* (2018.01)
*A61M 11/00* (2006.01)

(52) U.S. Cl.
CPC ....... *A61B 5/4839* (2013.01); *A61M 16/0003* (2014.02); *A61M 16/0051* (2013.01); *A61M 16/0066* (2013.01); *A61M 16/026* (2017.08); *A61M 16/1005* (2014.02); *A61M 16/1075* (2013.01); *A61M 16/12* (2013.01); *A61M 16/16* (2013.01); *G16H 40/63* (2018.01); *A61M 11/00* (2013.01); *A61M 16/0069* (2014.02); *A61M 16/125* (2014.02); *A61M 16/161* (2014.02); *A61M 2016/0033* (2013.01); *A61M 2202/0208* (2013.01); *A61M 2205/3303* (2013.01); *A61M 2205/3334* (2013.01); *A61M 2205/3368* (2013.01); *A61M 2205/3375* (2013.01); *A61M 2230/06* (2013.01); *A61M 2230/20* (2013.01); *A61M 2230/205* (2013.01); *A61M 2230/42* (2013.01); *A61M 2230/43* (2013.01); *A61M 2230/432* (2013.01); *A61M 2230/60* (2013.01)

(56) References Cited

U.S. PATENT DOCUMENTS

| | | |
|---|---|---|
| 2006/0266355 A1 | 11/2006 | Misholi et al. |
| 2008/0236582 A1* | 10/2008 | Tehrani ............... A61M 16/024 128/204.22 |
| 2009/0050152 A1 | 2/2009 | Iobbi |
| 2011/0067697 A1 | 3/2011 | Lellouche et al. |
| 2014/0158124 A1 | 6/2014 | L'Her et al. |
| 2014/0290658 A1* | 10/2014 | Schindhelm ......... A61B 5/4866 128/204.23 |
| 2015/0265796 A1* | 9/2015 | Miller ................. A61M 16/109 261/142 |

OTHER PUBLICATIONS

European Communication pursuant to Article 94(3) EPC, for EP Application No. 16852933.7, dated Oct. 28, 2020.
European Search Report, for EP Application No. 16852933.7, dated May 10, 2019.

* cited by examiner

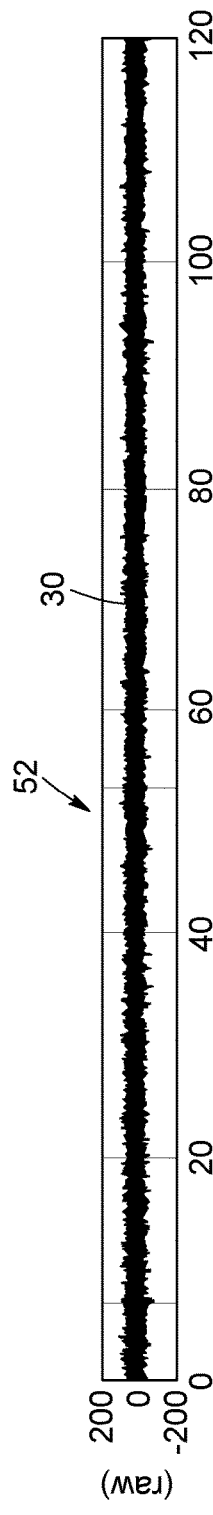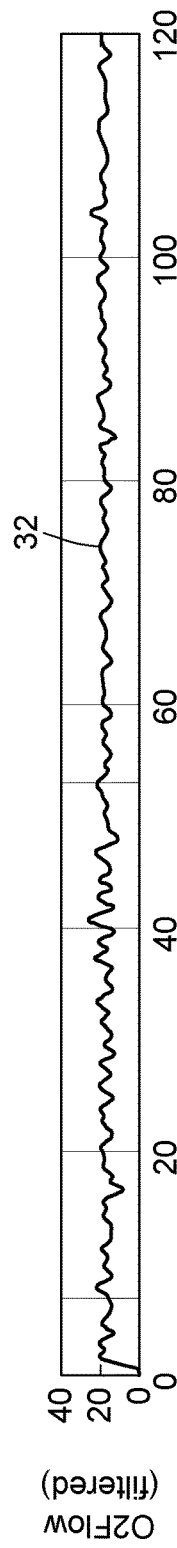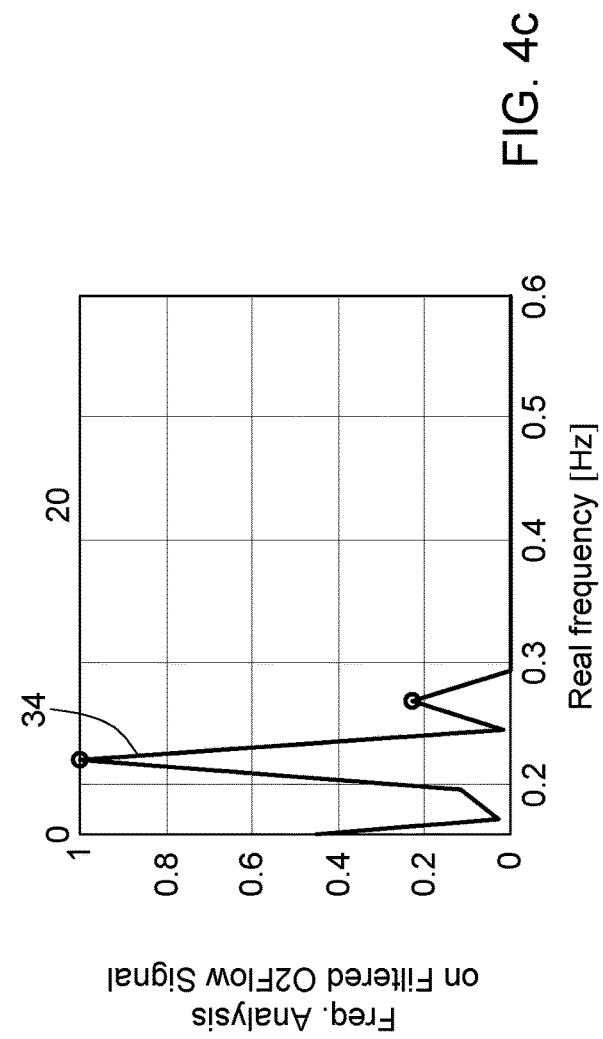
FIG. 4a
FIG. 4b
FIG. 4c

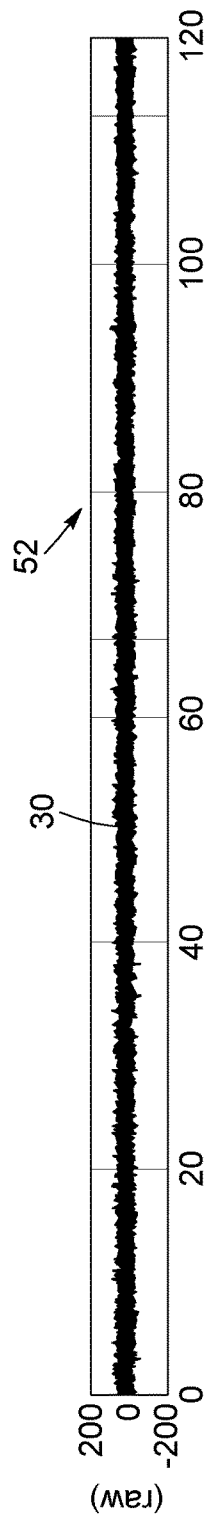
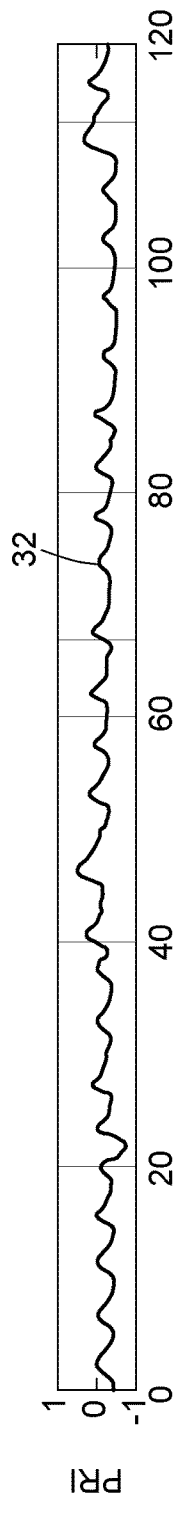
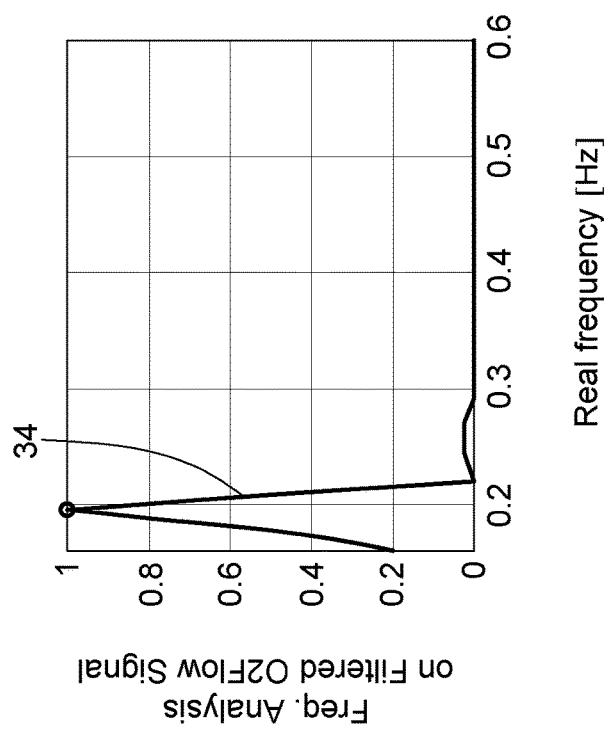
FIG. 5a
FIG. 5b
FIG. 5c

METHOD FOR DELIVERY OF BREATHING GAS TO A PATIENT AND SYSTEM FOR PERFORMING SAME

CROSS REFERENCE TO RELATED APPLICATION

This application claims the benefit under 35 U.S.C. § 119(e) of U.S. provisional patent application No. 62/237,252 which was filed on Oct. 5, 2015. The entirety of the aforementioned application is herein incorporated by reference.

TECHNICAL FIELD OF THE INVENTION

The present invention relates to the field of breathing assistance systems and methods. More particularly, it relates to a method for delivery of a breathing gas to a patient, where both the fraction of inspired oxygen ($FiO_2$) and the flowrate of the breathing gas are adjusted automatically, to a system for performing same and to improved methods for measuring and/or adjusting supply parameters of the breathing gas.

BACKGROUND

Several types of breathing assistance systems and methods for delivering a breathing gas to a patient are known to those skilled in the art. For example and without being limitative, it is well known to provide a flowrate of breathing gas, including oxygen, to patients having respiratory problems.

When performed adequately, such flowrate of breathing gas can be beneficial to a patient's condition. However, the supply of a breathing gas to a patient can also have adverse effects on its condition when inappropriate parameters, such as the breathing gas flowrate and/or the doses of oxygen, are used in the supply of the breathing gas. Unfortunately, such inappropriate parameters are often found during clinical use of breathing gas with flowrate administration. As a result, patient can suffer from hyperoxia, for example, due to deficient manual adjustment of doses and/or flowrate by clinical staff in charge of the patient.

Another issue with breathing assistance is that it is often not rapidly stopped when no longer required, which can lead to the increase of indirect hospital stay of the patient.

Yet another issue with breathing assistance is that the measured physiological parameter(s) used for controlling the supply parameters of the breathing gas can have a substantially low accuracy and/or be determined from low quality signal generated from the measuring material, which can lead to improper supply parameters of the breathing gas.

Yet another issue of known breathing assistance systems is that, in cases where humidification of the breathing gas is performed, there is a risk of overhumidity and a risk of condensation in the material providing the breathing gas to the patient, which is undesirable.

Yet another issue of known breathing assistance systems is that if a quality an oximeter signal used for measuring the oxygen saturation of the patient becomes low, the measure provided by the value of oxygen saturation provided by the oximeter can be unreliable and should be identified as requiring further verification in order to be used in an automatic adjustment system.

In view of the above, there is a need for an improved method and system for delivery of a breathing gas to a patient and an improved method for measuring and/or adjusting supply parameters of the breathing gas, which would be able to overcome or at least minimize some of the above-discussed prior art concerns.

BRIEF SUMMARY OF THE INVENTION

In accordance with a first general aspect, there is provided a method for controlling the delivery of a breathing gas to a patient. The method comprises: delivering a flow of breathing gas to a patient, the breathing gas having a breathing gas flowrate and a fraction of inspired oxygen; measuring an oxygen saturation level of the patient; determining a respiratory rate of the patient; automatically adjusting the fraction of inspired oxygen of the breathing gas based on the measured oxygen saturation level of the patient and a breathing gas flowrate set-point; and automatically adjusting the breathing gas flowrate set-point based on the determined respiratory rate of the patient.

In an embodiment, a weaning value of the fraction of inspired oxygen is defined and the step of determining the respiratory rate of the patient and the step of automatically adjusting the breathing gas flowrate set-point based on the determined respiratory rate of the patient are performed only while the fraction of inspired oxygen of the breathing gas is equal or below the weaning value of the fraction of inspired oxygen.

In an embodiment, the method further comprises initially setting the breathing gas flowrate set-point to an initial breathing gas flowrate set-point; comparing the fraction of inspired oxygen of the breathing gas to the weaning value of the fraction of inspired oxygen, and, if the fraction of inspired oxygen of the breathing gas is above the weaning value of the fraction of inspired oxygen, maintaining the breathing gas flowrate set-point at the initial breathing gas flowrate set-point.

In an embodiment, the method further comprises comparing the breathing gas flowrate to a breathing gas stopping threshold; and, if the breathing gas flowrate meets the breathing gas stopping threshold, halting delivering the breathing gas to the patient.

In an embodiment, measuring the oxygen saturation level of the patient is carried out by measuring a peripheral capillary oxygen saturation of the patient.

In an embodiment, measuring the saturation of peripheral oxygen of the patient is carried out using a pulse oximeter generating a pulse oximeter sensor signal and the method further comprises repeatedly assessing a quality of the pulse oximeter sensor signal.

In an embodiment, the pulse oximeter sensor signal is provided in packets of samples and the step of repeatedly assessing the quality of the pulse oximeter sensor signal comprises repeatedly: identifying minimal and maximal values of a plurality of groups of time consecutive packets of samples to determine a peak-to-peak amplitude value for each one of the groups of time consecutive packets of samples, each one of the groups containing at least one signal cycle; computing a median value of the peak-to-peak amplitude values of a plurality of latest peak-to-peak amplitude values; and assessing the quality of the pulse oximeter sensor signal based on the computed median value.

In an embodiment, the method further comprises eliminating extreme values from the determined peak-to-peak amplitude values prior to the computing of the median value.

In an embodiment, assessing the quality of the pulse oximeter sensor signal based on the computed median value is carried out using the function $$Q_{PPG} = \begin{cases} 0 & \text{if } \frac{\Delta P}{\Delta P_{ref}} < \lambda_L \\ 1 & \text{if } \frac{\Delta P}{\Delta P_{ref}} > \lambda_H \\ \frac{\frac{\Delta P}{\Delta P_{ref}} - \lambda_L}{\lambda_H - \lambda_L} & \text{otherwise} \end{cases}$$

wherein $\Delta P\_ref$ is a reference value and $\lambda\_L$ and $\lambda\_H$ are predefined threshold values.

In an embodiment, measuring the peripheral capillary oxygen saturation of the patient provides peripheral capillary oxygen saturation values and, the method further comprises repeatedly performing adjustment of the peripheral capillary oxygen saturation values used based on the assessed quality of the pulse oximeter sensor signal.

In an embodiment, a pulse oximetry signal quality threshold is defined and the method further comprises comparing the assessed quality of the pulse oximeter sensor signal to the pulse oximetry signal quality threshold and, if the assessed quality of the pulse oximeter sensor signal is above the signal quality threshold, carrying out the step of automatically adjusting the fraction of inspired oxygen of the breathing gas; otherwise, setting the fraction of inspired oxygen of the breathing gas to a safe fraction of inspired oxygen value otherwise.

In an embodiment, the safe fraction of inspired oxygen value ranges between about 40% and about 60%.

In an embodiment, the method further comprises humidifying the breathing gas.

In an embodiment, humidifying the breathing gas comprises maintaining a humidity of the breathing gas between about 30 mgH$_2$O/L and about 40 mgH$_2$O/L.

In an embodiment, humidifying the breathing gas comprises maintaining a relative humidity of the breathing gas below about 95%.

In an embodiment, humidifying the breathing gas comprises maintaining a relative humidity of the breathing gas between about 80% and about 90%.

In an embodiment, the method further comprises estimating the respiratory rate of the patient based on breathing gas flow signal data.

In an embodiment, estimating the respiratory rate of the patient based on the breathing gas flow signal data comprises: sensing a breathing gas flow to generate the breathing gas flow signal data; filtering the breathing gas flow signal data using a band-pass filter; performing at least one of an identification of the oscillation variation patterns and a an analysis of the repetitions of the oscillation variation patterns; and estimating the respiratory rate of the patient from the analysis of the filtered signal.

In an embodiment, filtering the breathing gas flow signal data using a band-pass filter comprises filtering the breathing gas flow signal data using a band-pass filter from about 0.08 Hz to about 0.7 Hz.

In an embodiment, the method further comprises adjusting the parameters of the band-pass filter for filtering the breathing gas flow signal data using the estimated respiratory rate.

In accordance with another general aspect, there is further provided a method for controlling the delivery of a breathing gas to a patient. The method comprises: delivering a flow of breathing gas to a patient, the breathing gas having an initial breathing gas flowrate set-point and a fraction of inspired oxygen; comparing the fraction of inspired oxygen to a fraction of inspired oxygen threshold value; and comparing the breathing gas flowrate to a breathing gas stopping threshold. If the fraction of inspired oxygen is above the fraction of inspired oxygen threshold value, the method comprises measuring an oxygen saturation level of the patient; automatically adjusting the fraction of inspired oxygen of the breathing gas based on the measured oxygen saturation level of the patient and the initial breathing gas flowrate set-point; and maintaining the breathing gas flowrate at the initial breathing gas flowrate set-point. If the fraction of inspired oxygen is equal or below the fraction of inspired oxygen threshold value, the method comprises: determining a respiratory rate of the patient; automatically adjusting the breathing gas flowrate set-point based on the determined respiratory rate of the patient; measuring the oxygen saturation level of the patient; and automatically adjusting the fraction of inspired oxygen of the breathing gas based on the measured oxygen saturation level of the patient and the breathing gas flowrate set-point. If the breathing gas flowrate reaches the breathing gas stopping threshold, the method comprises stopping the delivery of the breathing gas to the patient.

In an embodiment, measuring the oxygen saturation level of the patient is performed by measuring a peripheral capillary oxygen saturation of the patient.

In an embodiment, measuring the saturation of peripheral oxygen of the patient is performed using a pulse oximeter generating a pulse oximeter sensor signal and the method further comprises repeatedly assessing a quality of a pulse oximeter sensor signal.

In an embodiment the oximeter signal is provided in packets of samples and wherein the step of repeatedly assessing the quality of the pulse oximeter sensor signal from the pulse oximeter comprises repeatedly: identifying minimal and maximal values of a plurality of groups of time consecutive packets of samples to determine a peak-to-peak amplitude value for each one of the groups of time consecutive packets of sample, each one of the groups containing at least one signal cycle; computing a median value of the peak-to-peak amplitude values of a plurality of latest peak-to-peak amplitude values; and assessing the quality of the pulse oximeter sensor signal based on the computed median value.

In an embodiment, the method further comprises eliminating extreme values from the determined peak-to-peak amplitude values prior to computing the median value.

In an embodiment, assessing the quality of the pulse oximeter sensor signal based on the computed median value is carried out using the function $$Q_{PPG} = \begin{cases} 0 & \text{if } \frac{\Delta P}{\Delta P_{ref}} < \lambda_L \\ 1 & \text{if } \frac{\Delta P}{\Delta P_{ref}} > \lambda_H \\ \frac{\frac{\Delta P}{\Delta P_{ref}} - \lambda_L}{\lambda_H - \lambda_L} & \text{otherwise} \end{cases}$$

wherein $\Delta P\_ref$ is a reference value and $\lambda\_L$ and $\lambda\_H$ are predefined threshold values.

In an embodiment, measuring the peripheral capillary oxygen saturation of the patient provides peripheral capillary oxygen saturation values and, the method further comprises repeatedly performing adjustment of the peripheral capillary oxygen saturation values based on the assessed quality of the pulse oximeter sensor signal.

In an embodiment, a pulse oximetry signal quality threshold is defined and the method further comprises comparing the assessed quality of the pulse oximeter sensor signal to the pulse oximetry signal quality threshold and, if the assessed quality of the pulse oximeter sensor signal is above the signal quality threshold, carrying out the step of automatically adjusting the fraction of inspired oxygen of the breathing gas; otherwise, setting the fraction of inspired oxygen of the breathing gas to a safe fraction of inspired oxygen value otherwise.

In an embodiment, the safe fraction of inspired oxygen value ranges between about 40% and about 60%.

In an embodiment, the method further comprises the step of humidifying the breathing gas.

In an embodiment, humidifying the breathing gas comprises maintaining a humidity of the breathing gas between about 30 mgH$_2$O/L and about 40 mgH$_2$O/L.

In an embodiment, humidifying the breathing gas comprises maintaining a relative humidity of the breathing gas below about 95%.

In an embodiment, humidifying the breathing gas comprises maintaining a relative humidity of the breathing gas between about 80% and about 90%.

In an embodiment, the method further comprises estimating the respiratory rate of the patient based on breathing gas flow signal data.

In an embodiment, estimating the respiratory rate of the patient based on the breathing gas flow signal data comprises: sensing a breathing gas flow to generate the breathing gas flow signal data; filtering the breathing gas flow signal data using a band-pass filter; performing at least one of an identification of the oscillation variation patterns and a an analysis of the repetitions of the oscillation variation patterns; and estimating the respiratory rate of the patient from the analysis of the filtered signal.

In an embodiment, filtering the breathing gas flow signal data using a band-pass filter comprises filtering the breathing gas flow signal data using a band-pass filter from about 0.08 Hz to about 0.7 Hz.

In an embodiment, the method further comprises adjusting the parameters of the band-pass filter for filtering the breathing gas flow signal data using the estimated respiratory rate.

In accordance with another general aspect, there is also provided a system for delivering a flow of breathing gas to a patient. The system comprises: an ambient air dispenser and a supplemental gas supply cooperating to supply a breathing gas having a breathing gas flowrate set point and a fraction of inspired oxygen to the patient, each one of the ambient air dispenser and the supplemental gas supply including at least one actuator to respectively vary the ambient air flowrate supplied by the ambient air dispenser and the supplemental flowrate supplied by the supplemental gas supply; an oxygen saturation sensor measuring an oxygen saturation level of the patient; a respiratory rate sensor determining a respiratory rate of the patient; and a control unit operatively connected to the oxygen saturation sensor, the respiratory rate sensor, the actuator of the ambient air dispenser and the actuator of the supplemental gas supply, the control unit automatically adjusting the ambient air flowrate and the supplemental gas flowrate according to the measured oxygen saturation level and the breathing gas flowrate set-point and automatically adjusting the breathing gas flowrate set-point according to the determined respiratory rate.

In an embodiment, the control unit comprises: a first control sub-unit operatively connected to the oxygen saturation sensor, the actuator of the ambient air dispenser and the actuator of the supplemental gas supply, the first control sub-unit adjusting the ambient air flowrate and the supplemental gas flowrate according to the measured oxygen saturation level and the breathing gas flowrate set-point; and a second control sub-unit operatively connected to the respiratory rate sensor and the first control sub-unit, the second control sub-unit automatically adjusting the breathing gas flowrate set-point according to the determined respiratory rate.

In an embodiment, the oxygen saturation sensor comprises a pulse oximeter measuring a peripheral capillary oxygen saturation of the patient.

In an embodiment, the respiratory rate sensor is configured to acquire breathing gas flow signal data and the system further comprises a signal processing module in data communication with the respiratory rate sensor and the control unit, the signal processing module receiving the breathing gas flow signal data from the respiratory rate sensor and performing signal processing on the flow signal data to estimate the respiratory rate of the patient therefrom.

In an embodiment, the ambient air dispenser includes a ventilator having a turbine and wherein the respiratory rate sensor is operatively connected to the turbine of the ventilator and configured to acquire the breathing gas flow signal data therefrom.

In an embodiment, the supplemental gas supply includes an oxygen supply.

In an embodiment, the system further comprises a breathing gas humidifier automatically configured to adjust the humidification of the breathing gas based on the fraction of inspired oxygen and flowrate of the breathing gas.

In accordance with another general aspect, there is further provided a method for automatically adjusting a humidity of a breathing gas delivered to a patient. The method comprises: delivering a flow of breathing gas to a patient, the breathing gas having a breathing gas flowrate, a fraction of inspired oxygen and a humidity level; measuring an oxygen saturation level of the patient; determining a respiratory rate of the patient; automatically adjusting the fraction of inspired oxygen of the breathing gas based on the measured oxygen saturation level of the patient; automatically adjusting the breathing gas flowrate based on the determined respiratory rate of the patient; and automatically adjusting the humidity level of the breathing gas based on the fraction of inspired oxygen of the breathing gas and the breathing gas flowrate, the humidity level being maintained above about 30 mgH$_2$O/L and a relative humidity being maintained below about 95%.

In an embodiment, automatically adjusting the humidity level of the breathing gas comprises maintaining the humidity level between about 30 mgH$_2$O/L and about 40 mgH$_2$O/L.

In an embodiment, automatically adjusting the humidity level of the breathing gas comprises maintaining the relative humidity between about 80% and about 90%.

In an embodiment, the method further comprises monitoring additional gas humidity impacting factors including at least one of an initial temperature of the breathing gas, an initial humidity of the breathing gas, an ambient temperature and a temperature in the system for delivering the breathing gas and automatically adjusting the humidity level of the breathing gas based on the additional gas humidity impacting factors.

In an embodiment, the method further comprises adjusting a temperature of the breathing gas based on the fraction of inspired oxygen of the breathing gas and the breathing gas flowrate.

In an embodiment, adjusting the temperature of the breathing gas comprises maintaining the temperature of the breathing gas above about 30° C.

In accordance with another general aspect, there is further provided a method for repeatedly assessing a quality of a pulse oximeter sensor signal from a pulse oximeter signal provided in packets of samples. The method comprises: identifying minimal and maximal values of a plurality of groups of time consecutive packets of samples to determine a peak-to-peak amplitude value for each one of the groups of time consecutive packets of samples, each one of the groups containing at least one signal cycle; computing a median value of the peak-to-peak amplitude values of a plurality of latest peak-to-peak amplitude values; and assessing the quality of the pulse oximeter sensor signal based on the computed median value.

In an embodiment, the method further comprises eliminating extreme values from the determined peak-to-peak amplitude values prior to the computing the median value.

In an embodiment, assessing the quality of the pulse oximeter sensor signal based on the computed median value is carried out using the function $$Q_{PPG} = \begin{cases} 0 & \text{if } \frac{\Delta P}{\Delta P_{ref}} < \lambda_L \\ 1 & \text{if } \frac{\Delta P}{\Delta P_{ref}} > \lambda_H \\ \frac{\frac{\Delta P}{\Delta P_{ref}} - \lambda_L}{\lambda_H - \lambda_L} & \text{otherwise} \end{cases}$$

wherein $\Delta P\_ref$ is a reference value and $\lambda\_L$ and $\lambda\_H$ are predefined threshold values.

In an embodiment, measuring the peripheral capillary oxygen saturation of the patient provides peripheral capillary oxygen saturation values and the method further comprises repeatedly performing adjustment of the peripheral capillary oxygen saturation values used based on the assessed quality of the pulse oximeter sensor signal.

In an embodiment, a pulse oximetry signal quality threshold is defined and the method further comprises comparing the assessed quality of the pulse oximeter sensor signal to the pulse oximetry signal quality threshold and, if the assessed quality of the pulse oximeter sensor signal is above the signal quality threshold, carrying out the step of automatically adjusting the fraction of inspired oxygen of the breathing gas; otherwise, setting the fraction of inspired oxygen of the breathing gas to a safe fraction of inspired oxygen value otherwise.

In accordance with another general aspect, there is further provided, a method for estimating a physiological information of a patient based on an acquired breathing gas flow signal data, the method comprising: filtering the acquired breathing gas flow signal data using a band-pass filter to obtained a filtered signal; analysing the filtered signal to identify repetitions of oscillation variation patterns; and estimating the physiological information of the patient from the analysis of the filtered signal.

In an embodiment, the physiological information of the patient comprises one of the patient respiratory effort, the patient respiratory rate variability, the patient respiratory signal, the patient respiratory phases and the patient respiratory rate.

In an embodiment, the physiological information of the patient comprises the patient respiratory rate.

In an embodiment, filtering the acquired breathing gas flow signal data using the band-pass filter comprises filtering the acquired breathing gas flow signal data using a band-pass filter from about 0.08 Hz to about 0.7 Hz.

In an embodiment, analysing the filtered signal to identify repetitions of oscillation variation patterns comprises performing a frequency spectral analysis by consensus to define a consensus spectrum having a highest peak defining an average respiratory frequency.

In an embodiment, the method further comprises adjusting the parameters of the band-pass filter for filtering the breathing gas flow signal data using the estimated respiratory rate.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which:

FIGS. 4a to 4c are graphical representations of a processed breathing gas flow signal during extraction of a respiratory rate from the breathing gas flow signal wherein 4a shows the unprocessed breathing gas flow signal including a segment of interest; 4b shows the filtered flow signal including the segment of interest; and 4c shows the processed flow signal showing the segment of interest.

FIGS. 5a to 5c are graphical representations of a processed signal during extraction of a respiratory rate from the breathing flow signal, wherein 5a shows the unprocessed breathing gas flow signal including another segment of interest; 5b shows the filtered flow signal including the other segment of interest; and 5c shows the analysed flow signal showing the other segment of interest.

DETAILED DESCRIPTION

In the following description, the same numerical references refer to similar elements. The embodiments, geometrical configurations, materials mentioned and/or dimensions shown in the figures or described in the present description are embodiments only, given solely for exemplification purposes.

Moreover, although the embodiments of the system and method for delivery of a breathing gas to a patient, the method for the physiological parameters of the patient based on an acquired flow signal and the method for assessing a quality of an oximeter signal consist of certain components and/or configurations as explained and illustrated herein, not all of these components are essential and thus should not be taken in their restrictive sense. It is to be understood, as also apparent to a person skilled in the art, that other suitable components and cooperation thereinbetween, as well as other suitable configurations, may be used for the system and method for delivery of a breathing gas to a patient the method for the physiological parameters of the patient based on an acquired flow signal and the method for assessing a quality of an oximeter signal, as will be briefly explained herein and as can be easily inferred herefrom by a person skilled in the art.

Figure 1:
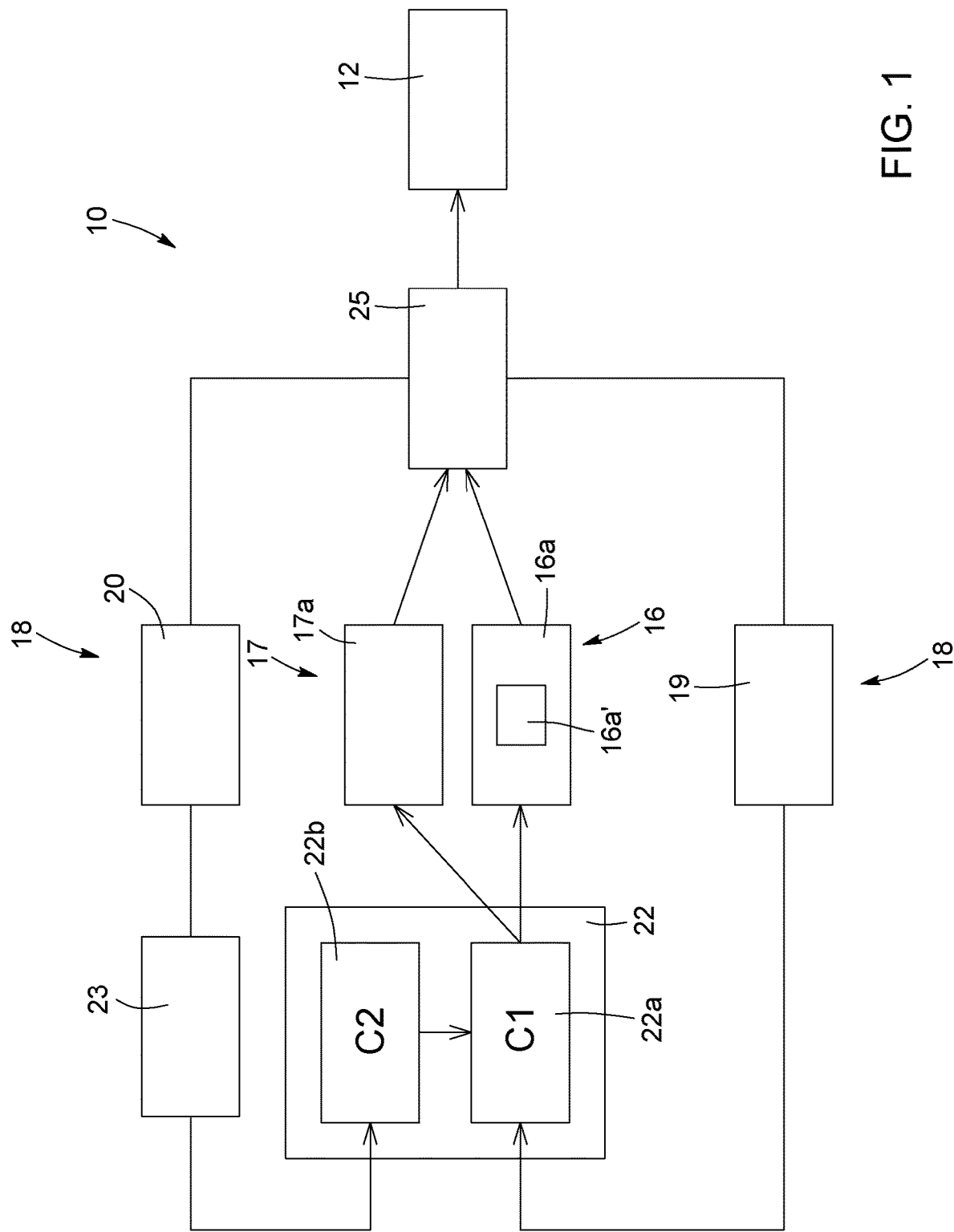
FIG. 1 is a schematic representation of a system for delivery of a breathing gas to a patient, in accordance with an embodiment.
Figure 2:
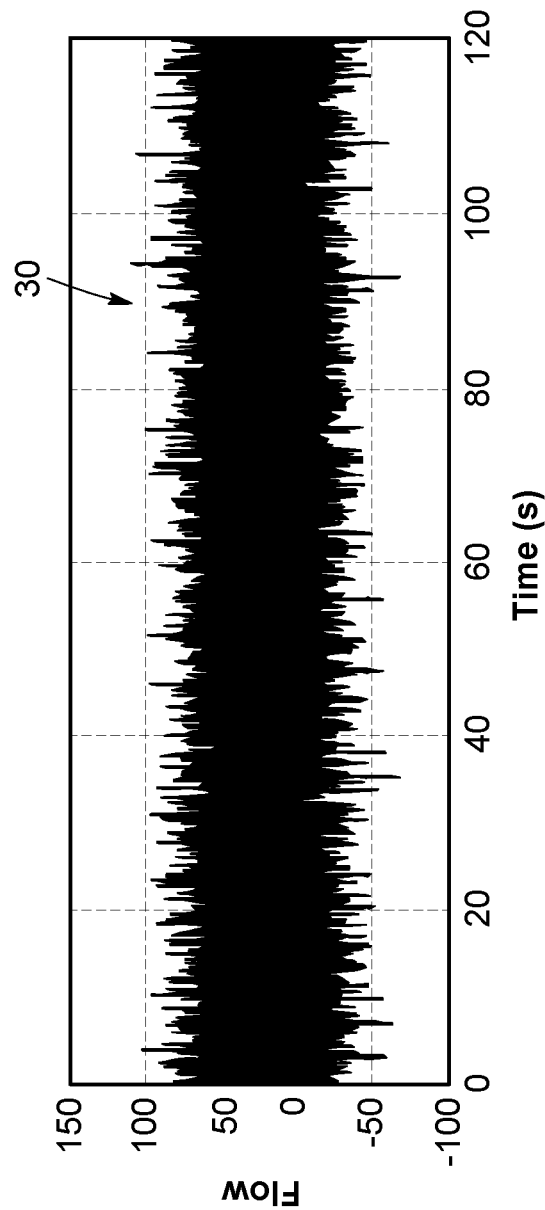
FIG. 2 is a graphical representation of a measured breathing gas flow signal.

Referring generally to FIG. 1, in accordance with one embodiment, there is provided a system 10 for administering a breathing gas to a patient 12. In the embodiment shown, the system 10 includes an ambient air dispenser 16, a supplemental gas supply 17, at least one physiological parameter sensor 18 and a control unit 22. The ambient air dispenser 16 and the supplemental gas supply 17 can be connected to a gas administration device (not shown), such as, for example and without being limitative, a facial mask or a nasal cannula (not shown) with the necessary connecting tubes, to administer the breathing gas to the patient 12. In an embodiment, the breathing gas includes oxygen and is administered to the patient 12 at a high flow (i.e. at a flow between about 10 l/min and about 100 l/min). In an embodiment, the breathing gas includes a mixture of ambient air and oxygen, i.e. air with higher oxygen content (above 21% (v/v)). Typically, the breathing gas is an oxygen-enriched air having a $FiO_2$ (i.e. fraction or percentage of oxygen in the breathing gas) greater than about 0.21.

The ambient air dispenser 16 and the supplemental gas supply 17 cooperate to provide the breathing gas to be dispensed to the patient 12. In the embodiment shown, the ambient air dispenser 16 includes a ventilator 16a having a turbine 16a' and providing a flow of ambient air and the supplemental gas supply 17 includes an oxygen supply 17a, such as, for example and without being limitative, a pressurized oxygen tank. The oxygen supply 17a provides supplemental oxygen to the flow of ambient air from the ventilator 16a, in order to generate the breathing gas. Each one of the ambient air dispenser 16 and the supplemental gas supply 17 includes at least one actuator (not shown). The actuators of the ambient air dispenser 16 and the supplemental gas supply 17 respectively vary the ambient air flowrate supplied by the ambient air dispenser 16 and the oxygen flowrate supplied by the supplemental gas supply 17. In a non-limitative embodiment, the actuator of the ambient air dispenser 16 can be a variable speed motor operatively connected to a fan of the ventilator 16a. In an alternative embodiment, the actuator of the ambient air dispenser 16 can also be dampers positioned to selectively dampen the airflow generated by the ventilator 16a. Similarly, in a non-limitative embodiment, the actuator of the supplemental gas supply 17 can be one or more adjustable valve(s) controllable to vary the supplemental gas flowrate. Thus, the flow of ambient air from the ventilator 16a and/or the flow of oxygen from the oxygen supply 17a can be varied, using the respective actuators, in order to generate a breathing gas having an adequate $FiO_2$ and be dispensed at an appropriate flowrate.

One skilled in the art will understand that, in alternative embodiments, other devices providing a mixture of ambient air and oxygen can be used in the system 10 for administering the breathing gas to a patient 12, instead of the above-mentioned ambient air dispenser 16 including a ventilator 16a and/or the above-mentioned supplemental gas supply 17 including an oxygen supply 17a.

One skilled in the art will understand that the at least one physiological parameter sensor(s) 18 can measure a plurality of physiological parameters of the patient 12. The physiological parameter sensor(s) 18 can be physical sensors measuring the respective physiological parameter on the patient or a virtual (soft) sensor estimating the respective physiological parameter using other measured variables. For instance and without being limitative, the at least one physiological parameters can measure oxygen-dependent physiological parameters, such as pulse oximetry, pulse rate, respiratory rate, end tidal carbon dioxide ($CO_2$) level, breathing pattern, or the like.

In the embodiment shown, the at least one physiological parameter sensor 18 includes an oxygen saturation sensor 19, such as, for example and without being limitative a pulse oximeter measuring the peripheral capillary oxygen saturation ($SpO_2$) (i.e. an estimation of the oxygen saturation level) of the patient. One skilled in the art will understand that, in an alternative embodiment, the oxygen saturation sensor 19 can measure the $SpO_2$ using a sensor different than the above-mentioned pulse oximeter or from a combination of sensors different therefrom.

In the embodiment shown, the at least one physiological parameter sensor 18 also includes a respiratory rate sensor 20 measuring or estimating the respiratory rate of the patient 12. As will be described in more details below, the respiratory rate sensor 20 can be a physical sensor, or a virtual (or soft) sensor estimating the respiratory rate from other measured variables. In an embodiment where the respiratory rate sensor 20 is a physical sensor, the respiratory rate sensor 20 can be an assembly including strain gauges placed along the patient's chest to detect when the patient inhales and exhales, or other physical device allowing measure of the respiratory rate of the patient.

Thus, in the embodiment shown, the measured physiological parameters include the $SpO_2$ and the respiratory rate. One skilled in the art will however understand that, in an alternative embodiment, the measured physiological parameter could differ from the $SpO_2$ and the respiratory rate.

Referring to FIGS. 1. to 5c, in an embodiment where the respiratory rate sensor 20 includes a virtual sensor, the respiratory rate can be estimated using the virtual sensor and based on breathing gas flow signal data acquired, for example and without being limitative, at an output of the system 10 by a separate flow sensor (not shown) or internally at a turbine of the ventilator 16a for ambient air, at the oxygen valve of the oxygen supply 17a, at an air-oxygen mixer of the ambient air dispenser 16, or the like.

In the embodiment of FIG. 1, the respiratory rate sensor 20 is configured to acquire breathing gas flow signal data and the system 10 comprises a signal processing module 23 in data communication with the respiratory rate sensor 20 and the control unit 22. The signal processing module 23 receives the breathing gas flow signal data from the respiratory rate sensor 20 and performs signal processing on the flow signal data to estimate the respiratory rate of the patient therefrom. One skilled in the art will understand that, in an alternative embodiment where the respiratory rate sensor 20 is a physical sensor, the system can be free of signal processing module 23.

Indeed, referring to FIGS. 2 to 5c, the change of phase from inspiration to expiration produces changes in the characteristics of the airways of the patient, which is reflected by minor changes in the high flow of breathing gas administered to a patient 12. In response to these minor changes in the flow of breathing gas administered at high flow, the above-mentioned turbine of the ventilator 16a for ambient air, oxygen valve of the oxygen supply 17a, and/or air-oxygen mixer of the ambient air dispenser 16, reacts to maintain the output flow at the target value, which introduces small oscillation-style variations in a breathing gas flow signal 30 thereof. These small oscillation-style variations introduced in the breathing gas flow signal 30 are repeated for each respirator cycle of a patient. Hence, it is possible to accurately estimate the respiratory rate of the patient from the measured breathing gas flow signal 30, through identification and/or analysis of the repetition of these specific small oscillation-style variation patterns. However, as can be clearly seen in FIG. 2 which shows a typical breathing gas flow signal 30 measured from an internal physical sensor of the system 10, the repetition of these specific small oscillation-style variation patterns are usually fairly small and can be lost in the background noise and/or fluctuations of the breathing gas flow signal 30.

Figure 3:
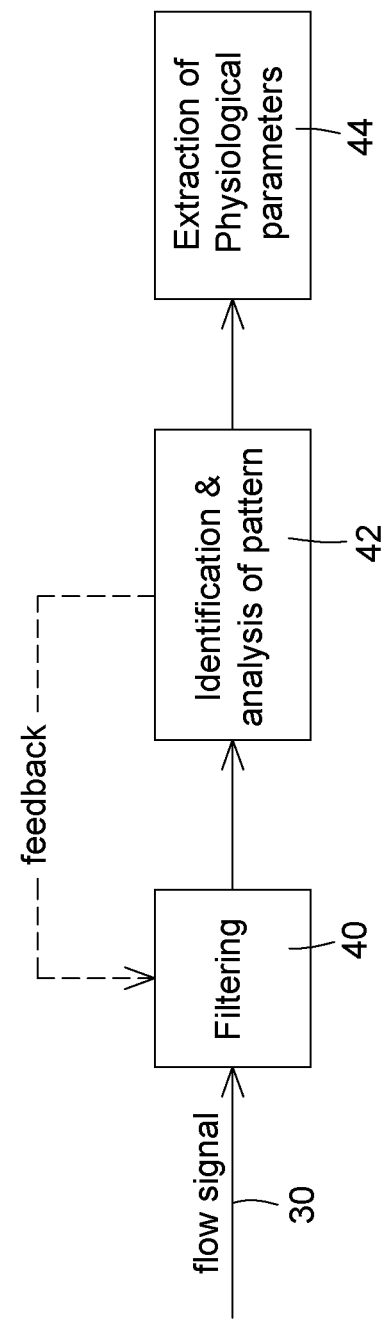
FIG. 3 is a flow chart showing the steps of a method for extracting patient physiological parameters from the breathing gas flow signal.

With reference to FIG. 3, in order to extract the repetition of the specific small oscillation-style variation patterns corresponding to the respiratory activity of the patient, sensing of a breathing gas flow to generate the breathing gas flow signal data, must initially be performed, Subsequently a signal processing (step 40) must therefore be performed on the breathing gas flow signal data defined by the flow signal 30. In an embodiment, the flow signal 30 can be filtered using a band-pass filter with parameters adjusted to the respiratory band. For example and without being limitative, in an embodiment, the breathing gas flow signal 30 can be filtered using a band-pass filter having a frequency band from about 0.08 Hz to about 0.7 Hz, which corresponds to a respiratory rate from about 4.8 breaths per minute (bpm) to about 42 bpm for an adult patient. One skilled in the art will understand that, in alternative embodiments, the frequency thresholds can be adjusted to adapt to the desired respiratory ranges associated with patients of different age, pathology, or the like. For example and without being limitative, in an alternative embodiment where a patient is a pediatric patient, the frequency band can be from about 0.2 Hz to about 1 Hz.

Once the breathing gas flow signal has been filtered to remove unnecessary components thereof, the filtered signal can be analyzed (step 42), for instance by signal processing, to identify the repetition of the respiration related oscillation-style variation patterns and/or analyze the repetitions of these patterns. The identified and/or analysed repetition of the respiration related oscillation-style variation patterns allows to derive physiological information of the patient therefrom (step 44). For example and without being limitative, in an embodiment, the analysis can include at least one of waveform restoration, segmentation of inspiration and expiration phases and estimation of statistical characteristics. In an embodiment, the physiological information includes the patient respiratory rate. In alternative embodiments, the physiological information can include other parameters such as, without being limitative, the patient respiratory effort, respiratory rate variability, respiratory signal, respiratory phases, etc.

Still, referring to FIG. 3, in the embodiment shown, the extracted information, such as the patient respiratory rate, can be used in a feedback loop for defining and/or adjusting the parameters of the band-pass filter used as a first step of the signal processing of the measured flow signal, thereby refining the filtering parameters iteratively. One skilled in the art will understand that, in an alternative embodiment (not shown), no feedback loop could be performed, such that the parameters of the band-pass filter used for the signal processing of the captured flow signal is solely defined by the human operator.

FIGS. 4a to 5c show the extraction of the respiratory rate of a patient, in a segment of interest 52 (delimited by the interval shown in the bold lined rectangle in FIGS. 4a, 4b, 5a and 5b) using the above described steps. The extraction is shown from a measured breathing gas flow signal 30 (shown in FIGS. 4a and 5a), to a filtered signal 32 (shown in FIGS. 4b and 5b), and the resulting analysed/processed signal 34 (shown in FIGS. 4c and 5c). In the embodiment shown, in order to measure the respiratory rate, a frequency spectral analysis by consensus was carried out, with the highest peak in the consensus spectrum defining the average respiratory frequency in the segment of interest of the measured flow signal. In an alternative embodiment, analysis by wavelet decomposition or an analysis by empirical mode decomposition could be performed.

One skilled in the art will understand that, in an alternative embodiment (not shown), the respiratory rate or other physiological parameter of the patient can be estimated by the signal processing module 23 based on signal data different from the breathing gas flow signal. For example and without being limitative, in an embodiment the respiratory rate can be estimated using data relative to the pulse oximetry plethysmographic curve acquired by the pulse oximeter. The respiratory rate can also be estimated using data obtained from an end tidal $CO_2$ sensor ($EtCO_2$ sensor) acquiring data relative to level of carbon dioxide released at the end of expiration by the patient, or other respiratory sensors acquiring data relative to the patient, such as variation of nasal temperature during inspiration/expiration, respiratory noises, electromyographic signals of nasal muscles, or the like. Moreover, one skilled in the art will understand that, in an embodiment, different estimation and/or measured methods can be combined to estimate and/or measure the respiratory rate or other physiological parameter of the patient.

Referring again to FIG. 1, in the embodiment shown, the control unit 22 further includes two control sub-units. A first control sub-unit 22a is operatively connected to at least one of the at least one physiological parameter sensor 18, the actuator(s) of the ambient air dispenser 16, and the actuator(s) of the supplemental gas supply 17. A breathing gas flowrate set-point is also supplied to the first control sub-unit 22a. The first control sub-unit 22a receives data from the at least one of the at least one physiological parameter sensor 18 and controls the actuator(s) of the ambient air dispenser 16 and the actuator(s) of the supplemental gas supply 17 based on the data received from the at least one of the at least one physiological parameter sensor 18.

In the embodiment shown, the first control sub-unit 22a is operatively connected to the oxygen saturation sensor 19, the actuator(s) of the ventilator 16a and the actuator(s) of the oxygen supply 17a. The first control sub-unit 22a receives data from the oxygen saturation sensor 19 (i.e. measured variable(s)), compares the data received to a predetermined oxygen saturation set-point, determines actuator set-points, i.e. the controlled variables, using the difference between the measured $SpO_2$ and the predetermined oxygen saturation set-point and the breathing gas flowrate set-point, and forwards the calculated controlled variables to the actuators to control the ventilator 16a and the oxygen supply 17a. For example and without being limitative, the actuator set-points can include a ventilator speed, a damper position, a motor speed, and the like (linked to an ambient air flowrate) and a valve position (linked to an oxygen flowrate).

Thus, the $FiO_2$ is automatically controlled by the first control sub-unit 22a according to the measured $SpO_2$ of the patient and the breathing gas flowrate set-point, as will be described in more details below in connection with the method for controlling the delivery of the breathing gas to the patient.

The second control sub-unit 22b is also operatively connected to at least one of the at least one physiological parameter sensor 18 to receive data therefrom. The second control sub-unit 22b is in data communication with the first control sub-unit 22a to adjust the breathing gas flowrate set-point based on the measured physiological parameter measured by the at least one physiological parameter sensor 18.

In the embodiment shown, the second control sub-unit 22b is operatively connected to the respiratory rate sensor 20 and is in data communication with the first control sub-unit 22a. The second control sub-unit 22b receives data from the respiratory rate sensor 20 and controls the breathing gas flowrate set-point based on the data received from the respiratory rate sensor 20. Thus, the flowrate of breathing gas supplied to the patient is automatically controlled by the second control sub-unit 22b according to the measure respiratory rate of the patient, as will be described in more details below in connection with the method for controlling the delivery of the breathing gas to the patient.

One skilled in the art will readily understand that different types of controllers, such as a proportional integral (PI) controller, a proportional integral derivative (PID) controller, control algorithms, or the like, can be implemented in the first control sub-unit 22a and the second control sub-unit 22b.

In an embodiment, the system 10 also includes a breathing gas humidifier 25 configured to humidify the breathing gas. The breathing gas humidifier 25 automatically adjusts the humidification of the breathing gas according to the respective quantity of ambient air and oxygen in the breathing gas (ambient air and oxygen having different humidity content) and according to the breathing gas flowrate.

Figure 6:
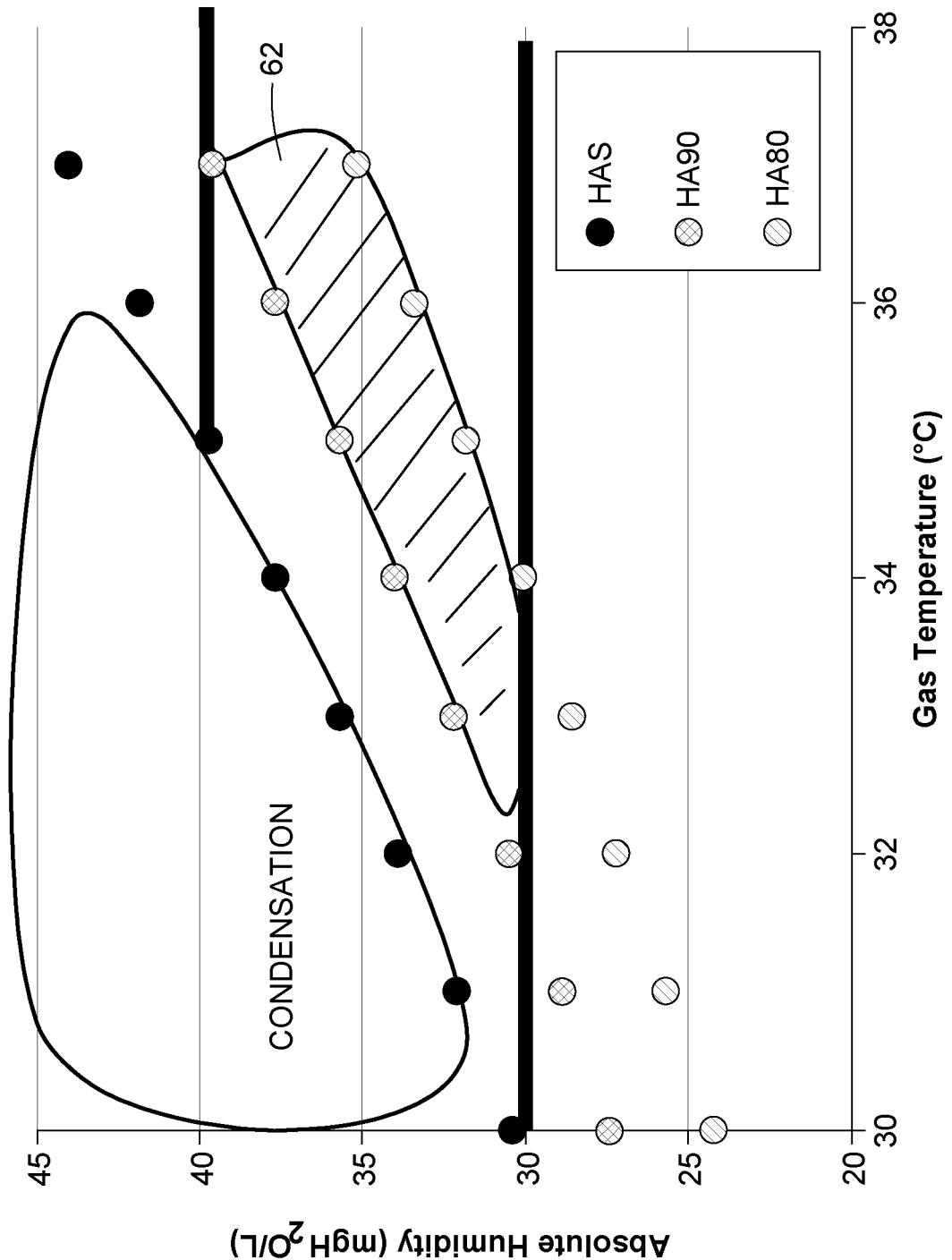
FIG. 6 is a graphical representation of a target range of humidity of the breathing gas according to the absolute humidity and gas temperature.

Referring to FIG. 6, in an embodiment the breathing gas humidifier 25 is operative to adjust the humidification of the breathing gas, while minimizing the risks of condensation (resulting from a relative humidity close to 100%), for example, to avoid rain flow in a nasal cannula of the patient or other gas administration device. As an example the breathing gas commonly includes a mixture of supplemental oxygen (or dry medical gas) having a humidity generally below 5 $mgH_2O/L$ and ambient air having a humidity generally in the range of about 15 $mgH_2O/L$. Hence, in the case of a high $FiO_2$ (high proportion of dry medical gas), the breathing gas will be very dry, while in the case of a low $FiO_2$ (low proportion of dry medical gas), the breathing gas will be moderately dry (i.e. proximate to 15 $mgH_2O/L$). In both cases, the overall desired humidity of the breathing gas will be below 30 $mgH_2O/L$, while the overall desired humidity of the breathing gas is generally above 30 $mgH_2O/L$ for high flow nasal therapy with temperature above 30° C.

As can be seen in FIG. 6 (see target humidity zone 62), in an embodiment the desired humidity of the breathing gas is between about 30 $mgH_2O/L$ and about 40 $mgH_2O/L$ for high flow nasal therapy with temperature above 30° C. Such a humidity level results in the relative humidity of the breathing gas being maintained below 95% (below HAS line in FIG. 6) to reduce the risk of condensation, even in the case of a decrease of temperature in the system (which would result in an increase in the relative humidity and an increase of the risk of condensation). In the embodiment shown, the relative humidity of the breathing gas is maintained between about 80% and about 90% (between HA80 line and HA90 line in FIG. 6).

One skilled in the art will understand that, in an embodiment, such humidity adjustment of the breathing gas can be performed through monitoring of gas humidity impacting factors such as and without being limitative, initial temperature of breathing gas, initial humidity of breathing gas, ambient temperature, temperature in the system, target temperature of breathing gas, target humidity of breathing gas and flow of breathing gas. In an embodiment, the initial temperature of the breathing gas, initial humidity of the breathing gas, ambient temperature and/or temperature in the system can be monitored using dedicated sensors (not shown). Using the above-mentioned humidity impacting factors, the energy required to heat and humidify either, each one of the ambient air and supplemental oxygen or the resulting breathing gas can be determined by the breathing gas humidifier 25 and the heating and humidification of the breathing gas can be adjusted by the gas humidifier 25, based thereon.

In an embodiment (not shown), the system 10 further includes a nebulizer configured to add a bronchodilator to the breathing gas.

Figure 7:
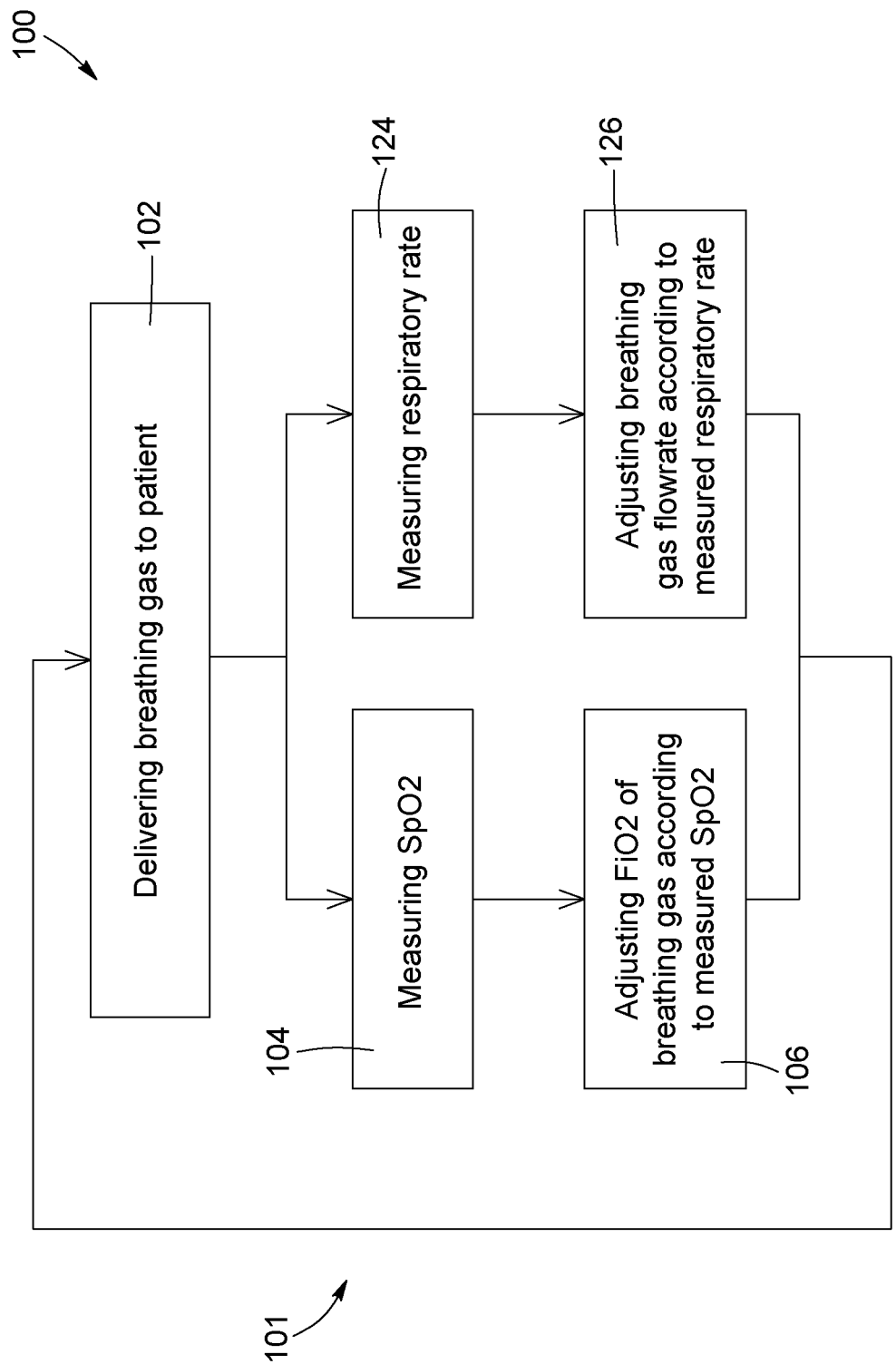
FIG. 7 is a flow chart showing the steps of a method for delivery of a breathing gas to the patient, according to an embodiment wherein the method includes a single $FiO_2$ and breathing gas flowrate adjustment loop.

Now referring to FIG. 7, a method 100 for controlling the delivery of the breathing gas to the patient will be described in more details below. The method is implemented by the system 10, wherein the control unit 22, including the first control sub-unit 22a and the second control sub-unit 22b, of the system 10 controls the ambient air dispenser 16, the supplemental gas supply 17, and the corresponding delivery of the breathing gas to the patient.

In accordance with an embodiment, the method 100 includes the initial step 102 of delivering a breathing gas to a patient. At step 102, the breathing gas has an initial breathing gas flowrate set-point. In an embodiment and without being limitative, the initial breathing gas flowrate set-point ranges between 20 l/min and 100 l/min. More particularly, in an embodiment, the initial breathing gas flowrate set-point is about 50 l/min. One skilled in the art will understand that the initial breathing gas flowrate set-point can be different for each patient depending on its physiological characteristics and condition and can be manually set by the physician or other operator of the system.

The method 100 also includes a breathing gas $FiO_2$ and flowrate adjustment loop 101. In the embodiment shown, the breathing gas $FiO_2$ and flowrate adjustment loop 101 includes the steps of measuring the respiratory rate of the patient 124, automatically adjusting the breathing gas flowrate set-point according to the measured respiratory rate 126, measuring the $SpO_2$ of the patient 104 and automatically adjusting the $FiO_2$ of the breathing gas according to the measured $SpO_2$ 106. In an embodiment, the breathing gas FiO$_2$ and flowrate adjustment loop 101 is performed repeatedly in order to adjust the FiO$_2$ of the breathing gas and the breathing gas flowrate set-point according to the measured physiological parameters of the patient (i.e. the measured SpO$_2$ and respiratory rate). It is appreciated that the control period can be the same or can be different for adjusting the FiO$_2$ of the breathing gas (i.e. the first control sub-unit 22a) and adjusting the breathing gas flowrate set-point (i.e. the second control sub-unit 22b). In an embodiment, the control period for adjusting the FiO$_2$ of the breathing gas (i.e. the first control sub-unit 22a) is shorter than the control period for adjusting the breathing gas flowrate set-point (i.e. the second control sub-unit 22b). For instance, in an embodiment, the FiO$_2$ of the breathing gas can be adjusted several times before modifying the breathing gas flowrate set-point (i.e. the second control sub-unit 22b).

In an embodiment, as will be described in more details below, the breathing gas flowrate set-point can be adjusted solely when at least one of the measured physiological parameter, such as the SpO$_2$ and/or the respiratory rate, or another variable, such as the FiO$_2$, meets a predetermined threshold. For instance and without being limitative, in an embodiment, the breathing gas flowrate set-point can be adjusted solely when the FiO$_2$ meets a predetermined FiO$_2$ threshold; the breathing gas flowrate set-point remaining at the initial breathing gas flowrate set-point until the predetermined FiO$_2$ threshold is met.

Figure 8:
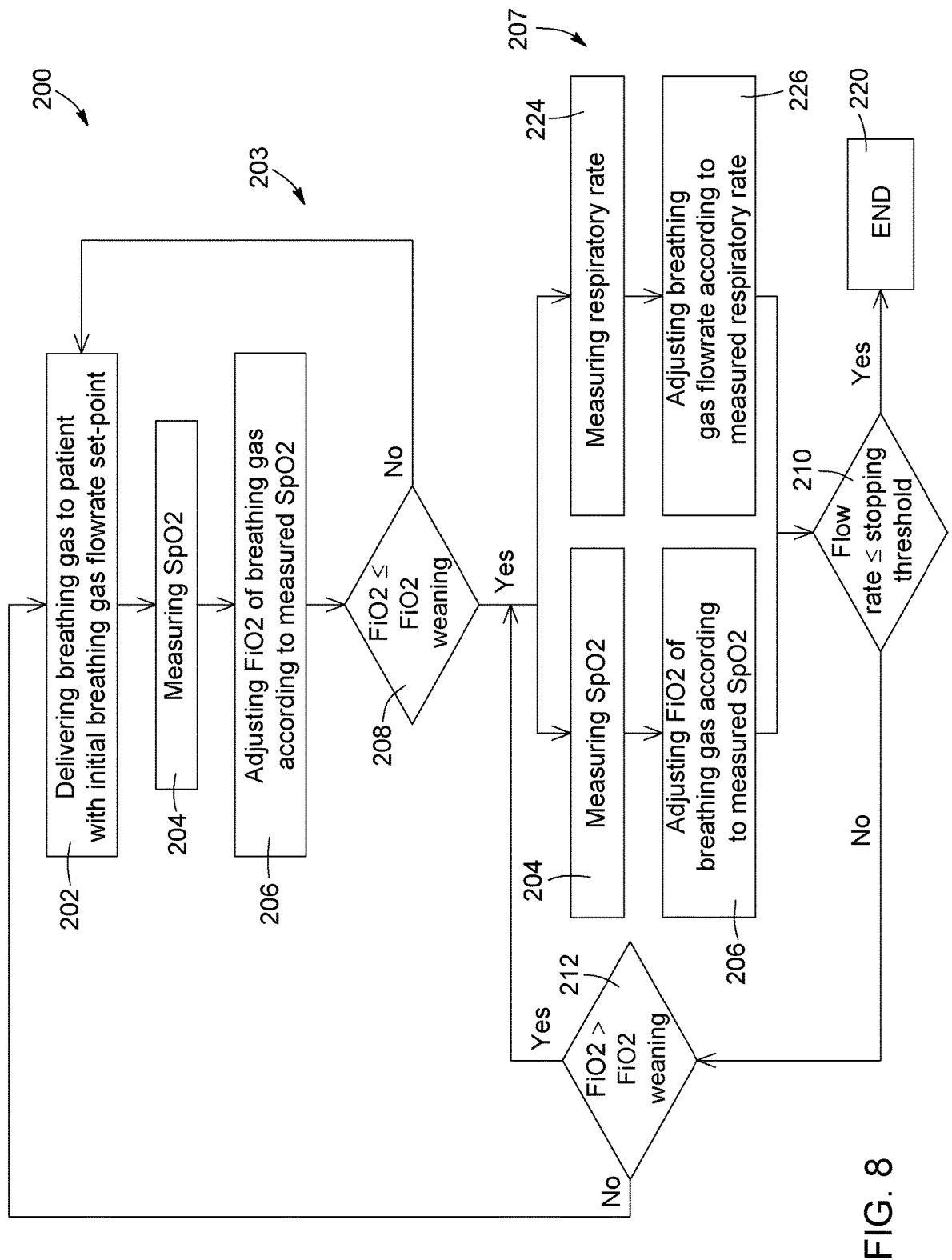
FIG. 8 is a flow chart of the method for delivery of a breathing gas to a patient, according to an alternative embodiment wherein the method includes a $FiO_2$ adjustment loop and a weaning loop.

Referring to FIG. 8, another embodiment of the method 100 for controlling the delivery of the breathing gas to the patient will be described in more details below, wherein like features are numbered with like reference number in the 200 series. The method 200 according to this alternative embodiment performs a weaning loop 207 (decrease of the breathing gas flowrate set-point), only when the FiO$_2$ reaches a weaning threshold (step 208). The weaning loop 207 is performed until the automatically controlled breathing gas flowrate set-point reaches a stopping threshold (step 210) indicative that the patient no longer requires breathing assistance and breathing assistance can be stopped (step 220). In the embodiment shown, during the weaning loop 207, if the FiO$_2$ of the breathing gas increases above the weaning threshold (step 212), the breathing gas flowrate set-point is adjusted and maintained at the initial breathing gas flowrate set-point until the FiO$_2$ again reaches the weaning threshold (step 208) and the weaning loop 207 can be reinitiated.

In more details, in the embodiment shown in FIG. 3, an initial step 202 of delivering a breathing gas to a patient is performed. Once again, at step 202, the breathing gas has an initial breathing gas flowrate set-point, with similar characteristics as those described in connection with step 102.

The method 202 includes a FiO$_2$ adjustment loop 203 performed repeatedly without any adjustment of the breathing gas flowrate set-point while the FiO$_2$ value is above the FiO$_2$ weaning threshold. In an embodiment and without being limitative, the FiO$_2$ weaning threshold ranges between about 40% and about 60%. One skilled in the art will understand that the FiO$_2$ weaning threshold can be different for each patient depending on its physiological characteristics and can be set by the physician or other operator of the system.

The FiO$_2$ adjustment loop 203 includes the steps of measuring the SpO$_2$ of the patient 204 and automatically adjusting the FiO$_2$ of the breathing gas according to the measured SpO$_2$ 206. In an embodiment, these steps are carried out by the control unit 22, and more particularly, the first control sub-unit 22a.

The method 200 further includes the weaning loop 207 performed once the FiO$_2$ value has reached the FiO$_2$ weaning threshold (as determined at step 208). The weaning loop 207 is initiated at the initial breathing gas flowrate set-point, as described above, and is repeatedly performed until either the breathing gas flowrate set-point reaches a stopping threshold (step 210) or the FiO$_2$ increases above the weaning threshold (step 212). If the breathing gas flowrate set-point reaches the stopping threshold (step 210), the breathing assistance is halted, the patient being determined to no longer require such assistance. If the FiO$_2$ increases above the weaning threshold (step 212), the breathing gas flowrate is adjusted to the initial breathing gas flowrate set-point and the FiO$_2$ adjustment loop 203 is performed until the FiO$_2$ value once again reaches the FiO$_2$ weaning threshold (step 208). Once again, when the FiO$_2$ value reaches the FiO$_2$ weaning threshold (step 208), the weaning loop 207 is initiated at the initial breathing gas flowrate set-point. In an embodiment, the steps for adjusting the breathing gas flowrate set-point are carried out by the control unit 22, and more particularly, the second control sub-unit 22b.

The weaning loop 207 includes the steps of measuring the SpO$_2$ of the patient 204 and automatically adjusting the FiO$_2$ of the breathing gas according to the measured SpO$_2$ 206. In addition, the weaning loop 207 includes the further steps of measuring the respiratory rate of the patient 224 and automatically adjusting the breathing gas flowrate set-point according to the measured respiratory rate 226. In an embodiment, the steps of measuring the respiratory rate of the patient 224 and automatically adjusting the breathing gas flowrate set-point according to the measured respiratory rate 226 are performed concurrently with the steps of measuring the SpO$_2$ of the patient 204 and automatically adjusting the FiO$_2$ of the breathing gas according to the measured SpO$_2$ 206.

As mentioned above, in the weaning loop 207, the control period can be the same or can be different for adjusting the FiO$_2$ of the breathing gas (i.e. the first control sub-unit 22a) and adjusting the breathing gas flowrate set-point (i.e. the second control sub-unit 22b).

One skilled in the art will easily understand that, in an alternative embodiment of the above described method 200, a SpO$_2$ weaning threshold or another threshold associated with a measured physiological parameter of the patient, or a combination thereof, can be used rather than a FiO$_2$ weaning threshold to determine when the weaning loop 207 can be initiated (step 208) and/or when the weaning loop 207 can be terminated (step 212). Similarly, a respiratory rate stopping threshold, or another threshold or combination of thresholds associated with a measured physiological parameter of the patient can be used rather than a flowrate stopping threshold, to determine when the breathing assistance is terminated.

As mentioned above in the description of the associated system 10, in the above described method 100, 200, in each one of the steps of automatically adjusting the FiO$_2$ in the breathing gas according to the measured SpO$_2$ 106, 206 and automatically adjusting the breathing gas flowrate according to the measured respiratory rate 126, 226, the automatic adjustment is performed via a comparison between the corresponding one of the measured SpO$_2$ and respiratory rate and a predetermined set-point thereof and subsequent control of the actuators of the ambient air dispenser 16 and supplemental gas supply 17.

In an embodiment (not shown), the method 100, 200, can also include the step of humidifying the breathing gas. In such an embodiment, the method, 100, 200 can include the step of automatically adjusting the humidification of the breathing gas according to the respective quantity of ambient air and/or oxygen in the breathing gas and/or according to the breathing gas flowrate, using the above-described steps for performing humidification using the breathing gas humidifier.

In another alternative embodiment, the method, 100, 200, can further include the step of adding a bronchodilator to the breathing gas. In such an embodiment, the method can include the step of automatically adjusting the bronchodilator flowrate.

The above described system 10 and method 100, 200 for delivery of a breathing gas to a patient can be used for numerous applications such as, without being limitative in emergency and intensive care for patients with hypoxemia (pneumonia, cardiogenic pulmonary edema, acute chronic obstructive pulmonary disease (COPD) exacerbations, or the like), in intensive care for patients with hypoxemia, in anesthesia recovery room for the monitoring of hypercapnia risk in awakening patients, in pulmonology and general wards for all patients under oxygen, in rehabilitation for patients with pulmonary insufficiency or cardiac failure, at home for patients with chronic respiratory insufficiencies requiring long-term oxygen therapy, or the like.

Advantageously, the proposed system 10 and method 100, 200 can optimize the time spent in the optimal $SPO_2$ interval while minimizing the oxygen flowrate, thereby allowing a substantial reduction in oxygen consumption and recovery time for patients.

Figure 9:
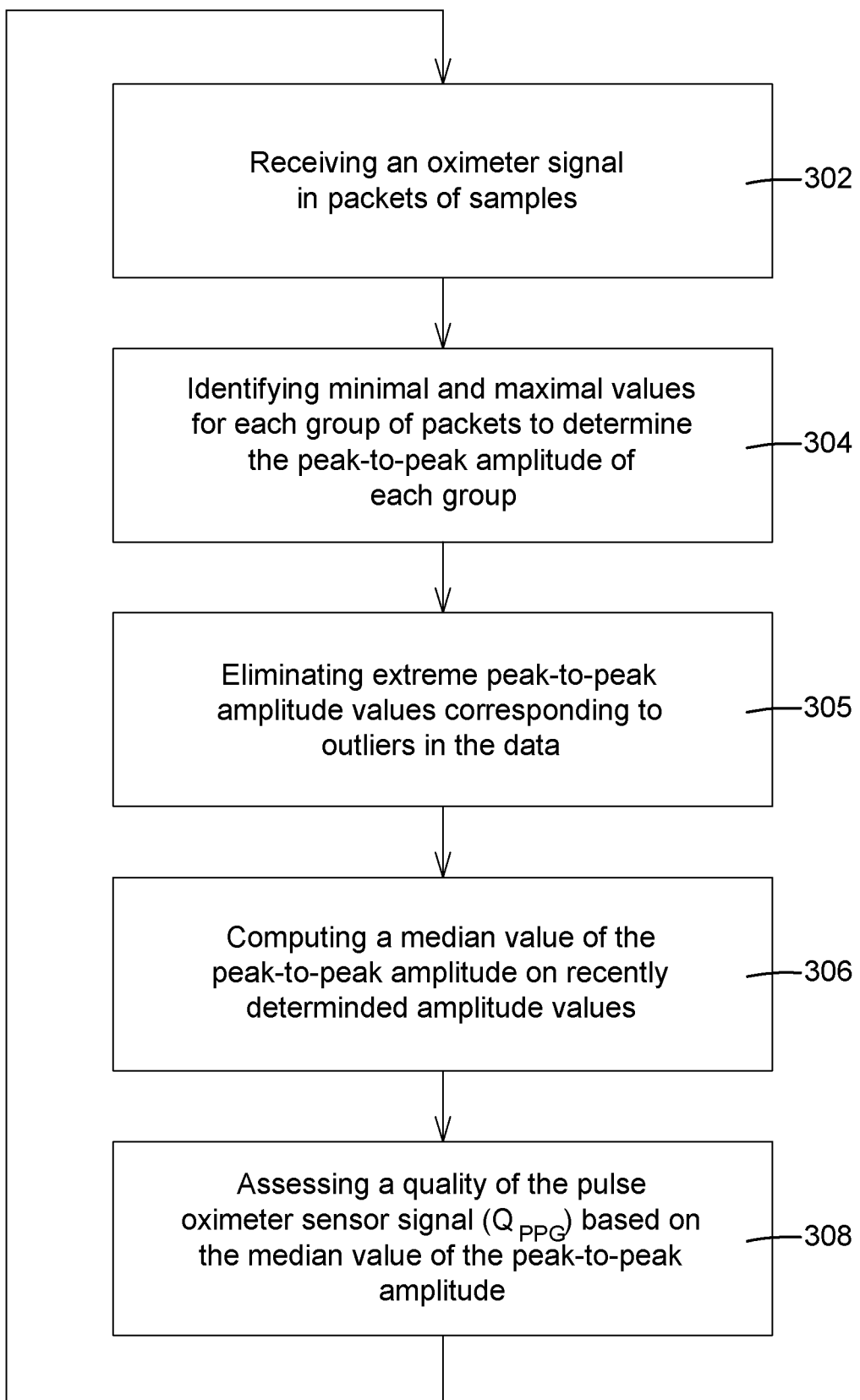
FIG. 9 is a flow chart of a method for assessing a quality of a pulse oximeter sensor signal, in accordance with an embodiment.

Referring to FIG. 9, a method for assessing a quality of the pulse oximeter sensor signal can further be provided. In an embodiment where the method for assessing a quality of the pulse oximeter sensor signal is provided, the method for controlling the delivery of the breathing gas to the patient can include the further step of performing adjustment of the $SpO_2$ values used for regulating the $FiO_2$ of the breathing gas, in view of an analysis of the assessed quality of the pulse oximeter sensor signal.

In an embodiment, the analysis of the quality of the pulse oximeter sensor signal can be performed through repeated analysis of the signal amplitude, substantially in real-time.

For example, in an embodiment where the oximeter signal comes in packets of samples (step 302), the analysis can be carried out on every group of N consecutive recorded packets (or time consecutive packets). For example and without being limitative, in an embodiment, the analysis can include the steps of identifying minimal and maximal values for each group of N packets to determine the peak-to-peak amplitude of each group (step 304) and computing a median value of the peak-to-peak amplitude on K recently determined (or latest) amplitude values (step 306).

In an embodiment, the determination of the median value of the peak-to-peak amplitude can be performed subsequently to an elimination of extreme peak-to-peak amplitude values corresponding to outliers in the data (step 305). For example and without being limitative, in an embodiment, between about 10% an about y % of extreme peak-to-peak amplitude values corresponding to outliers can be eliminated before proceeding to the computing of the median value of the peak-to-peak amplitude on the K recently determined (or latest) amplitude values, i.e. eliminating values over the $95^{th}$ percentile and below the $5^{th}$ percentile.

In an embodiment, the variable N corresponding to the number of packets is chosen such that the processed N consecutive packets contain at least one signal cycle, thereby avoiding under-estimation of cycle peak-to-peak amplitude. Moreover, in order to minimize the response time of the algorithm, the variable N should be as low as possible. The value of the variable N will be chosen according to the sampling frequency and the packet size. For example and without being limitative, in an embodiment, where the sampling frequency is about 75 sample/second, with a packet size of about 75 sample/packet, the variable N can be between about 1 and about 4.

In an embodiment, the variable K of the recently determined (or latest) amplitude value used for the computing of the median value of the peak-to-peak amplitude is high enough to minimize the influence of spontaneous abnormal amplitude values induced by artifacts, temporary loss of data, or the like. However, the variable K should not be too high in order to maintain the response time of the algorithm in an acceptable range for a continuous real-time monitoring framework. The value of the variable K will once again be chosen according to the sampling frequency and the packet size, and the chosen value of variable N. For example and without being limitative, in the embodiment, where the sampling frequency is about 75 sample/second, with a packet size of about 75 sample/packet, the variable K can be between about 3 and about 10.

In an embodiment, the above-mentioned median value of peak-to-peak amplitude, denoted below as $\Delta P$, can subsequently be used to assess the quality of the pulse oximeter sensor signal (step 308).

In an embodiment, the quality of the pulse oximeter sensor signal $Q_{PPG}$ is assessed as follows:

$$Q_{PPG} = \begin{cases} 0 & \text{if } \frac{\Delta P}{\Delta P_{ref}} < \lambda_L \\ 1 & \text{if } \frac{\Delta P}{\Delta P_{ref}} > \lambda_H \\ \frac{\frac{\Delta P}{\Delta P_{ref}} - \lambda_L}{\lambda_H - \lambda_L} & \text{otherwise} \end{cases}$$

where $\Delta P\_ref$ is a reference value, $\lambda\_L$ and $\lambda\_H$ are two thresholds predefined with respect to a patient category.

In an alternative embodiment, the quality of the pulse oximeter sensor signal $Q_{PPG}$ can be assessed using alternative smooth quality functions.

For example, in an embodiment, the quality of the pulse oximeter sensor signal $Q_{PPG}$ can be assessed using a sigmoid function:

$$Q_{PPG} = \frac{1}{1 + \exp\left(-\alpha \frac{\frac{\Delta P}{\Delta P_{ref}} - \frac{\lambda_H - \lambda_L}{2}}{\lambda_H - \lambda_L}\right)}$$

where parameter $\alpha$ is a constant used to control the curvature of the function at the boundaries.

For example, in another embodiment, the quality of the pulse oximeter sensor signal $Q_{PPG}$ can be assessed using a smooth step function:

$$Q_{PPG} = 3\left(\frac{\frac{\Delta P}{\Delta P_{ref}} - \lambda_L}{\lambda_H - \lambda_L}\right)^2 - 2\left(\frac{\frac{\Delta P}{\Delta P_{ref}} - \lambda_L}{\lambda_H - \lambda_L}\right)^3$$

In an embodiment, the assessed quality of the pulse oximeter sensor signal $Q_{PPG}$ can further be adjusted according to the presence or absence of artifact in the pulse oximeter sensor signal, during the observing interval.

In an embodiment, the assessed quality of the pulse oximeter sensor signal $Q_{PPG}$ can further be incorporated within an existing signal quality index. For example, in an embodiment, the assessed quality of the pulse oximeter sensor signal $Q_{PPG}$ can be incorporated within the signal quality index provided by a Nonin OEM3 acquisition card, as follows:

$$Q^{overall} = \frac{Q^{OEM3}}{3} \times Q_{PPG}$$

In an embodiment, once the quality of the pulse oximeter sensor signal $Q_{PPG}$ has been assessed, the assessed signal quality can be used in the adjustment of the $FiO_2$ of the breathing gas. In an embodiment, a signal quality threshold can be defined and the adjustment of the $FiO_2$ in the breathing gas can be performed only when the assessed quality of the pulse oximeter sensor signal $Q_{PPG}$ is above the signal quality threshold. In such an embodiment, the adjustment of the $FiO_2$ is performed while the assessed quality of the pulse oximeter sensor signal $Q_{PPG}$ is above the signal quality threshold.

If the assessed quality of the pulse oximeter sensor signal $Q_{PPG}$ decreases below the signal quality threshold, the $FiO_2$ can be automatically set to a safe $FiO_2$ value, for example based on historical data of the patient and an alarm can be raised. In an embodiment, the safe $FiO_2$ value can range between about 40% and about 60%. One skilled in the art will understand that the safe $FiO_2$ value can be different for each patient depending on its physiological characteristics and can be set by the physician or other operator of the system, or be determined by the system using historical data. For example and without being limitative, in an embodiment, the safe $FiO_2$ can be the currently used $FiO_2$ if the mean $SpO_2$ of the last minute before it fell below the signal quality threshold is within a target $SpO_2$ value range, and the current $FiO_2$ augmented by between about 20% and 30% if the mean $SpO_2$ of the last minute before it fell below the signal quality threshold is below the target $SpO_2$ value range.

In an embodiment, the $SpO_2$ values can also be adjusted according to the assessed quality of the pulse oximeter sensor signal $Q_{PPG}$, through determination of a relation between an underestimation of the $SpO_2$ values and the assessed quality of the pulse oximeter sensor signal $Q_{PPG}$, for example modeled and regressed using practical data gathered by the system.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

The invention claimed is:

1. A system for delivering a flow of breathing gas to a patient, the system comprising:
    an ambient air dispenser and a supplemental gas supply cooperating to supply a breathing gas having a breathing gas flowrate set point and a fraction of inspired oxygen to the patient, each one of the ambient air dispenser and the supplemental gas supply including at least one actuator to respectively vary the ambient air flowrate supplied by the ambient air dispenser and the supplemental flowrate supplied by the supplemental gas supply;
    an oxygen saturation sensor measuring an oxygen saturation level of the patient;
    a respiratory rate sensor determining a respiratory rate of the patient; and
    a control unit operatively connected to the oxygen saturation sensor, the respiratory rate sensor, the actuator of the ambient air dispenser and the actuator of the supplemental gas supply, the control unit automatically adjusting the ambient air flowrate and the supplemental gas flowrate according to the measured oxygen saturation level and the breathing gas flowrate set-point and automatically adjusting the breathing gas flowrate set-point according to the determined respiratory rate;
    wherein the breathing gas flowrate set-point is adjusted solely when the fraction of inspired oxygen meets a predetermined fraction of inspired oxygen threshold, the breathing gas flowrate set-point remaining at an initial breathing gas flowrate set-point until the predetermined fraction of inspired oxygen threshold is met, the predetermined fraction of inspired oxygen threshold being a weaning threshold.

2. The system of claim 1, wherein the control unit comprises:
    a first control sub-unit operatively connected to the oxygen saturation sensor, the actuator of the ambient air dispenser and the actuator of the supplemental gas supply, the first control sub-unit adjusting the ambient air flowrate and the supplemental gas flowrate according to the measured oxygen saturation level and the breathing gas flowrate set-point; and
    a second control sub-unit operatively connected to the respiratory rate sensor and the first control sub-unit, the second control sub-unit automatically adjusting the breathing gas flowrate set-point according to the determined respiratory rate.

3. The system of claim 1, wherein the oxygen saturation sensor comprises a pulse oximeter measuring a peripheral capillary oxygen saturation of the patient.

4. The system of claim 1, wherein the respiratory rate sensor is configured to acquire breathing gas flow signal data, the system further comprising a signal processing module in data communication with the respiratory rate sensor and the control unit, the signal processing module receiving the breathing gas flow signal data from the respiratory rate sensor and performing signal processing on the flow signal data to estimate the respiratory rate of the patient therefrom.

5. The system of claim 4, wherein the ambient air dispenser includes a ventilator having a turbine and wherein the respiratory rate sensor is operatively connected to the turbine of the ventilator and configured to acquire the breathing gas flow signal data therefrom.

6. The system of claim 1, wherein the supplemental gas supply includes an oxygen supply.

7. The system of claim 1, further comprising a breathing gas humidifier automatically configured to adjust the humidification of the breathing gas based on the fraction of inspired oxygen and flowrate of the breathing gas.

8. The system of claim 1 wherein the weaning threshold ranges between 40% and 60%.

9. The system of claim 1, wherein the system is halted if the breathing gas flowrate set-point reaches a stopping threshold.

10. The system of claim 1, wherein, if the fraction of inspired oxygen of the breathing gas increases above the weaning threshold after having met predetermined fraction of inspired oxygen threshold, the breathing gas flowrate set-point is adjusted and maintained at the initial breathing gas flowrate set-point until the fraction of inspired oxygen reaches the predetermined fraction of inspired oxygen.

11. The system of claim 1, further comprising a signal processing module receiving the breathing gas flow signal from the respiratory rate sensor and performing signal processing on the breathing gas flow signal to estimate the respiratory rate of the patient, the breathing gas flow signal being filtered using a band-pass filter with parameters adjusted to the respiratory band, analyzed to identify a repetition of a respiration related oscillation-style variation patterns, and used to carry out a frequency spectral analysis by consensus, wherein a highest peak in the consensus spectrum defines the respiratory rate.

12. The system of claim 1, wherein the measured oxygen saturation level, used for regulating the fraction of inspired oxygen, is adjusted in view of an analysis of an assessed quality of a pulse oximeter sensor signal.

13. The system of claim 1, wherein an assessed signal quality of a pulse oximeter sensor signal is used in the adjustment of the fraction of inspired oxygen of the breathing gas.

14. The system of claim 1, wherein the adjustment of the fraction of inspired oxygen in the breathing gas is performed only when the assessed quality of the pulse oximeter sensor signal is above a signal quality threshold.

15. The system of claim 14, wherein the fraction of inspired oxygen is automatically set to a safe fraction of inspired oxygen when the assessed quality of the pulse oximeter sensor signal decreases below the signal quality threshold, the safe fraction of inspired oxygen ranging between 40% and 60%.

* * * * *